(12) United States Patent
Han et al.

(10) Patent No.: US 7,974,786 B2
(45) Date of Patent: Jul. 5, 2011

(54) VISUALIZATION METHOD OF RNA PSEUDOKNOT STRUCTURES

(75) Inventors: Kyungsook Han, Inchon (KR); Yan A. Byun, Inchon (KR)

(73) Assignee: INHA-Industry Partnership Institute, Inchon (KR)

( * ) Notice: Subject to any disclaimer, the term of this patent is extended or adjusted under 35 U.S.C. 154(b) by 952 days.

(21) Appl. No.: 10/852,872

(22) Filed: May 24, 2004

(65) Prior Publication Data

US 2005/0042640 A1     Feb. 24, 2005

(30) Foreign Application Priority Data

May 27, 2003   (KR) .................. 10-2003-0033804

(51) Int. Cl.
| | |
|---|---|
| *G06F 19/00* | (2011.01) |
| *G06F 17/60* | (2006.01) |
| *G01N 33/48* | (2006.01) |

(52) U.S. Cl. ............................. 702/19; 703/2

(58) Field of Classification Search .................. None
See application file for complete search history.

(56) References Cited

U.S. PATENT DOCUMENTS 7,136,760 B2 * 11/2006 Han et al. ................... 702/20

OTHER PUBLICATIONS

Lee et al., New Representation and Algorithm for Drawing RNA Structure with Pseudoknots, Springerlinked Jan. 1, 2002, Springer-Verlag Berlin Heidelberg, pp. 191-201.*

* cited by examiner

*Primary Examiner* — Jason Sims
(74) *Attorney, Agent, or Firm* — Klarquist Sparkman LLP

(57) ABSTRACT

The present invention relates to a visualization method of RNA pseudoknot structures for more efficiently and clearly visualizing all types of RNA pseudoknot structures including H-types in the form of a planar graph without edge-crossing so that the structures can be easily examined. The visualization method comprises reading the structure data in bracket view, identifying stem-loops and pseudoknots enclosed in bracket pairs from the input structure data, first computing the position and shape of a stem-loop contained in an identified pseudoknot to visualize the stem-loop, second computing the position and shape of the pseudoknot containing the calculated stem-loop to visualize the pseudoknot, third computing the position and shape of a stem-loop outside the computed pseudoknot, and inserting or connecting the visualized stem-loops into or to the pseudoknots to complete an RNA pseudoknot structure drawing.

6 Claims, 24 Drawing Sheets

| ((((( | :::: | [[[[[[[ | ::(((((:::::)))))::  | ))))) | :: | ((((( | :: | ]]]](((((:::::)))))]]]] | :: | ))))) |
|---|---|---|---|---|---|---|---|---|---|---|
| S1O | B1 | S2O | B2 | S1C | B4 | S3O | B3 | S2C | B5 | S3C |

FIG. 10

VISUALIZATION METHOD OF RNA PSEUDOKNOT STRUCTURES

CROSS REFERENCE TO RELATED APPLICATION

This application claims the benefit of Korean patent application no. 10-2003-0033804, filed May 27, 2003.

BACKGROUND OF THE INVENTION

1. Field of the Invention

The present invention relates to a visualization method of RNA pseudoknot structures, more particularly, which can more efficiently and clearly visualize an RNA pseudoknot structure in the form of a planar graph.

2. Description of the Prior Art

The visualization of a complex molecular structure helps the observer to understand the structure, and is a key component among the support tools available in the biosciences.

An RNA pseudoknot is a tertiary structural element formed when bases of a single-stranded loop pair with complementary bases outside the loop. Pseudoknots are not only widely occurring structural motifs in many kinds of RNA molecules but are also responsible for several important RNA functions. For example, pseudoknot structures present in coding regions of the RNA molecules can stimulate ribosomal frameshifting and translational read-through during elongation. In addition, pseudoknots in noncoding regions can initiate translation either by being part of the so-called Internal Ribosomal Entry Site (IRES) in the 5' noncoding region or by forming translational enhancers in the 3' noncoding region.

However, in the view of graph theory, the RNA secondary structure is a tree, whereas the RNA pseudoknot structure is a graph (and possibly a nonplanar graph) with inner cycles within the pseudoknot and possibly outer cycles formed between the pseudoknot and other structure elements. Thus, visualization of the RNA pseudoknot structure is more difficult than that of the RNA secondary structure.

Currently, there are many methods or programs developed for visualizing RNA secondary structures, but a visualization method or program of RNA pseudoknots has not been developed yet.

In prior art, RNA pseudoknots are often visualized manually either by connecting RNA pseudoknots together via line segments or by utilizing a graph edition function after visualizing the RNA secondary structure using a visualization program. In either case, visualizing RNA pseudoknots manually is difficult and the obtained results become rapidly more unsatisfactory as the size and complexity of the entire RNA structure increases.

FIGS. 1a to 1d are typical schematic representations of H-type pseudoknots visualized in a conventional visualization method of RNA pseudoknots. More particularly, FIG. 1a illustrates the most general H-type pseudoknot structure, wherein dotted lines represent the connection between bases in a hairpin loop and the bases in a 3'-end direction. In addition, FIGS. 1b to 1d illustrate H-type pseudoknot structures, in which loops 1 to 3 are omitted so that stems 1 and 2 are aligned in line. FIG. 1c is the most commonly occurring pseudoknot structure among the structures shown in the FIGS. 1b to 1d.

As shown in the FIGS. 1a to 1d, a pseudoknot structure drawn in a conventional method has many edge crossings, which reduce the readability of the drawings and make it difficult to follow the RNA sequence from end to end. Edge crossings are inevitable in these drawings in order to stack the two stems coaxially. However, the drawing of pseudoknots with secondary structure represents a topological structure rather than a geometric structure. That is, a drawing of this type is intended to represent the connectivity of bases, and therefore, the drawing should focus on making connectivity relations clear.

SUMMARY OF THE INVENTION

Therefore, the present invention has been contemplated to solve the foregoing problems of the prior art.

It is an object of the present invention to provide a visualization method of RNA pseudoknot structures, more particularly, which can more efficiently and clearly visualize all types of RNA pseudoknot structures including H-types in the form of a planar graph without edge-crossing so that the structures can be easily examined (FIGS. 2 and 3).

According to an aspect of the invention for realizing the object, there is provided a visualization method of RNA pseudoknot structures, the method comprising the following steps of: reading the structure data in bracket view; identifying stem-loops and pseudoknots enclosed in bracket pairs from the input structure data; first computing the position and shape of a stem-loop contained in an identified pseudoknot to visualize the stem-loop; second computing the position and shape of the pseudoknot containing the calculated stem-loop to visualize the pseudoknot; third computing the position and shape of a stem-loop outside the computed pseudoknot; and inserting or connecting the visualized stem-loops into or to the pseudoknots to complete an RNA pseudoknot structure drawing.

It is preferred that the identification step distinguishes a simple stem-loop without a stem-loop contained therein, a composite stem-loop containing at least one other stem-loop and a pseudoknot from one another (FIG. 5).

It is preferred that the first computation step comprises: stacking base pairs of a stem-loop on a vertical axis or y-axis to have the same y coordinate; computing a loop center C, a loop radius R and a base-to-base angle of loop α according to equations below:

$$2\alpha \cdot n = 2\pi => \alpha = \frac{\pi}{n}, \quad \sin(\alpha) = \frac{L/2}{R} => R = \frac{L}{2\sin(\alpha)},$$

and $\vec{C} = d \cdot \vec{N} + \vec{P_m}$, wherein n is the number of bases in the loop plus 2, L is the distance between a base pair and an adjacent base, $\vec{P_m}$ is the midpoint vector of the last base pair $p_1$ and $p_2$ of the stem $$\vec{P_m} = (x_m, y_m) = \frac{\vec{P_1} + \vec{P_2}}{2} = \left(\frac{x_1 + x_2}{2}, \frac{y_1 + y_2}{2}\right),$$

$x_1, x_2, y_1$ and $y_2$ are coordinates of the last base pair $p_1$ and $p_2$, d is the distance from the midpoint $P_m$ to the loop center C, that is, $\|\vec{C} - \vec{P_m}\| = R \sin(\theta) = R \sin(\pi/2 - \alpha)$, and N is the unit vector directed toward the loop center from the midpoint $P_m$; and arranging the stem-loop at an angle 2α on a circle of a radius R from a loop center C (FIG. 6).

In addition, the visualization method of RNA pseudoknot structures may further comprise the steps of: if the stem-loop processed in the first computation step is contained in other composite stem-loop, computing vectors s and p as in an equation below using sStart that is the position of the first base of a simple stem-loop before being connected to a composite stem-loop, sEnd that is the position of the last base of the simple-loop before being connected to the composite stem-loop, pStart that is the position of the first base of the simple stem-loop after being connected to the composite stem-loop and pEnd that is the position of the last base of the simple stem-loop after being connected to the composite stem-loop:

$$\vec{s} = \frac{\overrightarrow{sEnd} - \overrightarrow{sStart}}{\|\overrightarrow{sEND} - \overrightarrow{sStart}\|}, \text{ and } \vec{p} = \frac{\overrightarrow{pEnd} - \overrightarrow{pStart}}{\|\overrightarrow{pEND} - \overrightarrow{pStart}\|},$$

computing an angle b according to $b = \cos^{-1}(\vec{p} \cdot \vec{s})$ using the computed vectors s and p; rotating the stem-loop, which is to be contained in other composite stem-loop, for the angle b; and translating and inserting the rotated stem-loop into the corresponding composite stem-loop (FIG. 7).

It is preferred that the second computation step comprises: classifying the identified pseudoknot into stems and internal structure elements located between the stems; vertically arranging the stems so that each base pair has the same y coordinate; computing the position and shape of each internal structure element to visualize the internal structure element; and inserting the visualized internal structure element into a designated stem or between designated stems.

It is preferred that the classification step classifies the pseudoknot into at least one selected from group including: a first stem with the first base being connected to 5'-end, a second stem with the first base being connected to the last base of the first stem, a third stem with the first base being connected to the last base pair of the second stem and the last base being connected to 3'-end and first to fifth internal structure elements which are either unpaired bases located between the first to third stems or stem-loops.

It is also preferred that the first internal structure element is a structure element between an opening part of the first stem and an opening part of the second stem of the pseudoknot, wherein the second internal structure element is a structure element between an opening part of the second stem and a closing part of the first stem of the pseudoknot, wherein the third internal structure element is a structure element between a closing part of the second stem and an opening part of the third stem of the pseudoknot, wherein the fourth internal structure element is a structure element between a closing part of the first stem and an opening part of the third stem of the pseudoknot, and wherein the fifth internal structure element is a structure element between a closing part of the second stem and a closing part of the third stem of the pseudoknot.

It is preferred that the insertion step comprises: rotating stem-loops located in the opening part of the first stem, the first internal structure element and the opening part of the third stem 90° counterclockwise before insertion; horizontally flipping stem-loops in the opening part of the second stem and the second internal structure element and rotating the same 90° counterclockwise before insertion; rotating stem-loops in the closing part of the first stem, the fifth internal structure element and the closing part of the third stem 90° clockwise before insertion; and horizontally flipping stem-loops in the third internal structure elements, the fourth internal structure element and the closing part of the second stem and rotating the same 90° clockwise before insertion.

In addition, the visualization method of RNA pseudoknot structures may further comprise the steps of: adjusting positions of bases in either the opening part or the closing part of the inserted stem so that a pair of bases have the same y coordinate.

According to an aspect of the invention for realizing the object, there is provided a program for executing the aforedescribed visualization method of RNA pseudoknot structures.

BRIEF DESCRIPTION OF THE DRAWINGS

The above and other objects, features and other advantages of the present invention will be more clearly understood from the following detailed description taken in conjunction with the accompanying drawings, in which:

FIGS. 3a to 3e are schematic representations of other type pseudoknots visualized according to the present invention, in which FIG. 3a is a LL-type pseudoknot, FIG. 3b is an $HL_{out}$-type pseudoknot, FIG. 3c is an $HL_{in}$-type pseudoknot, FIG. 3d is a HH-type pseudoknot, and FIG. 3e is a HHH-type pseudoknot;

FIG. 10 illustrates structure data of the hypothetical pseudoknot shown in the FIG. 9;

DESCRIPTION OF THE PREFERRED EMBODIMENTS

The present invention provides a method for uniformly drawing all types of pseudoknots without edge-crossing. Finally, according to the present invention, several types of pseudoknot structures are drawn as shown in FIGS. 2a to 3e.

Figure 1A:
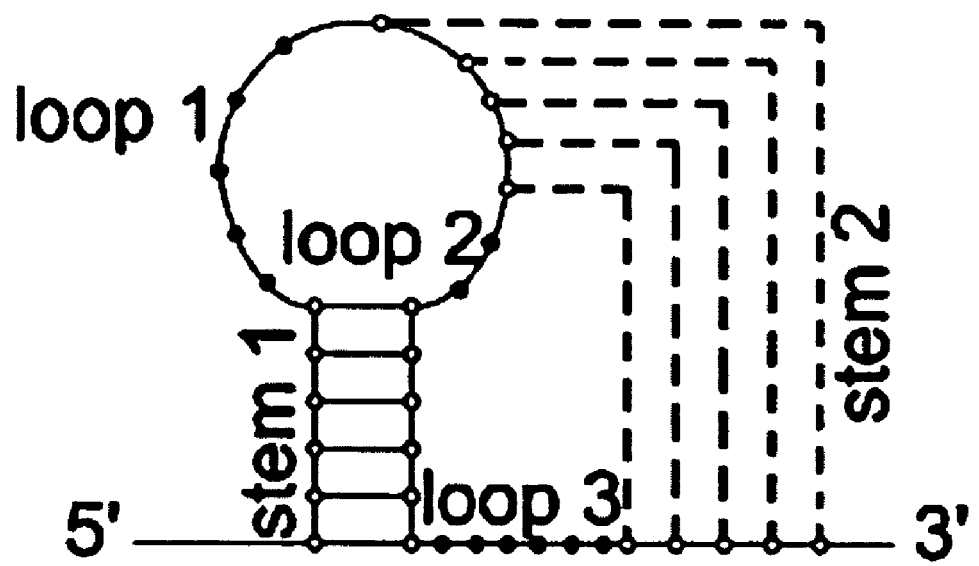
FIGS. 1a to 1d are schematic representations of H-type pseudoknots visualized according to conventional visualization methods of RNA pseudoknots.
Figure 1B:
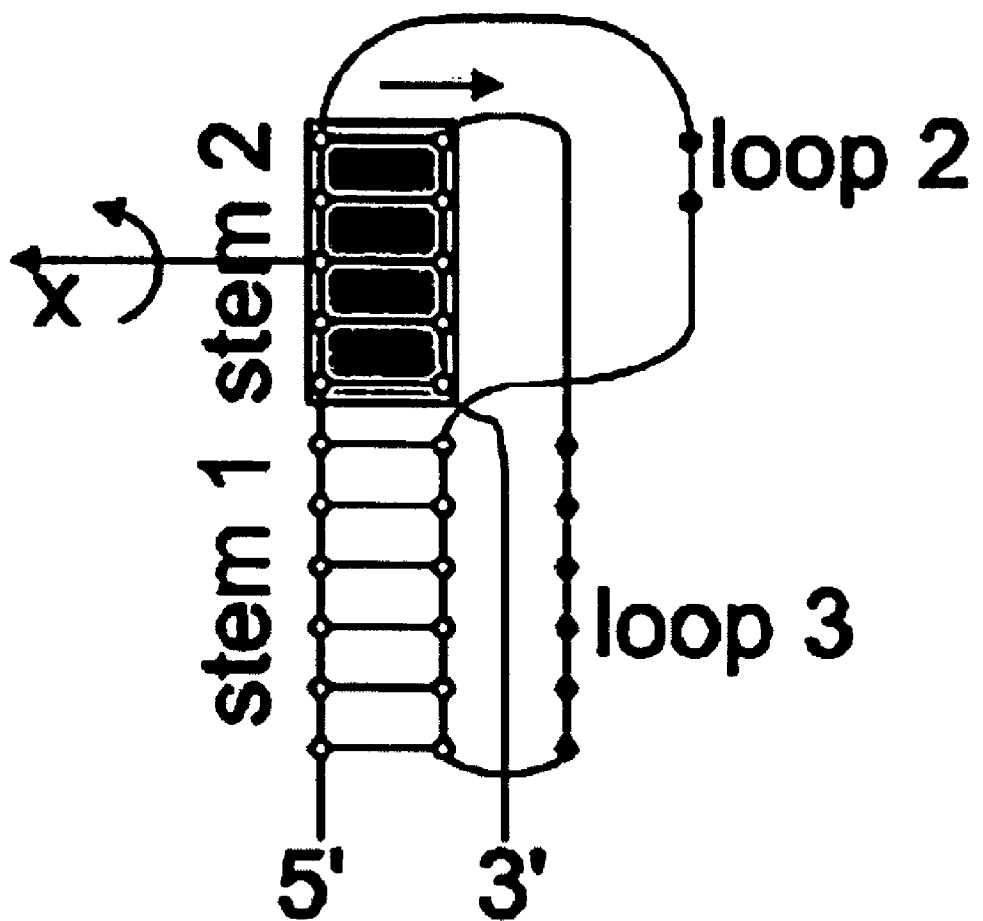
Figure 1C:
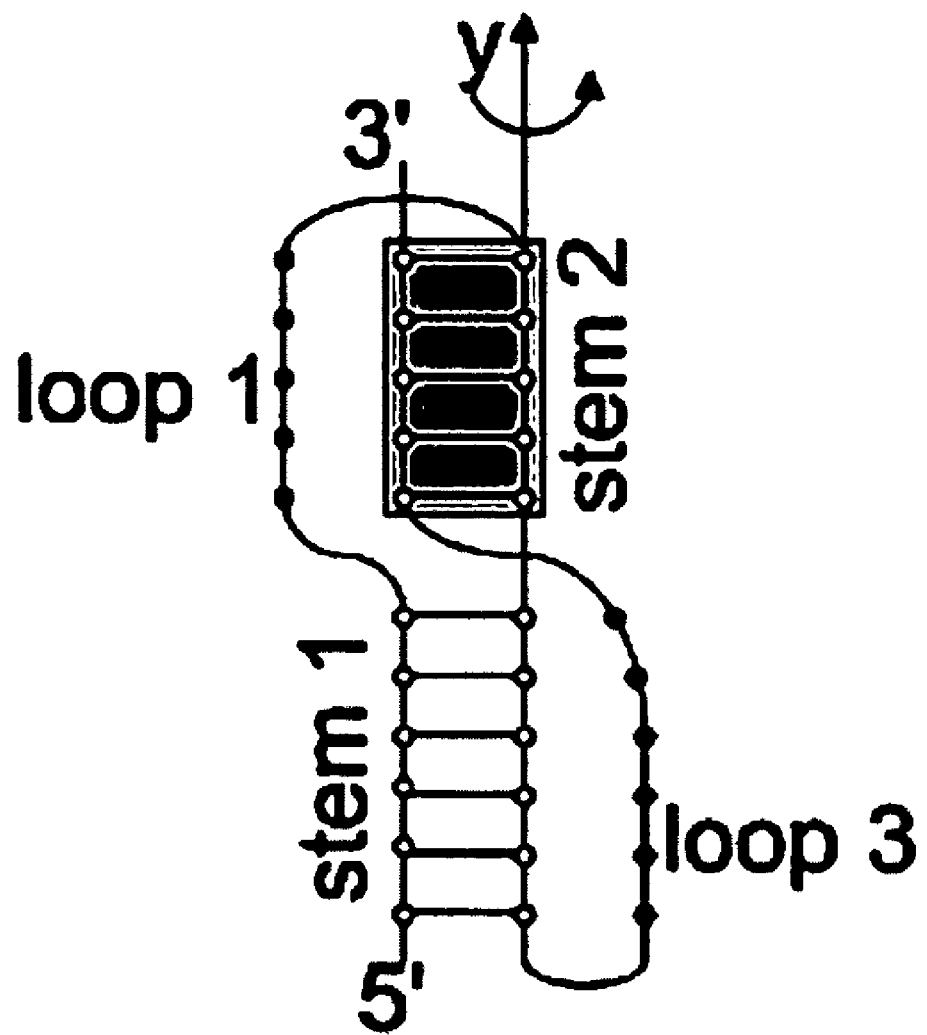
Figure 1D:
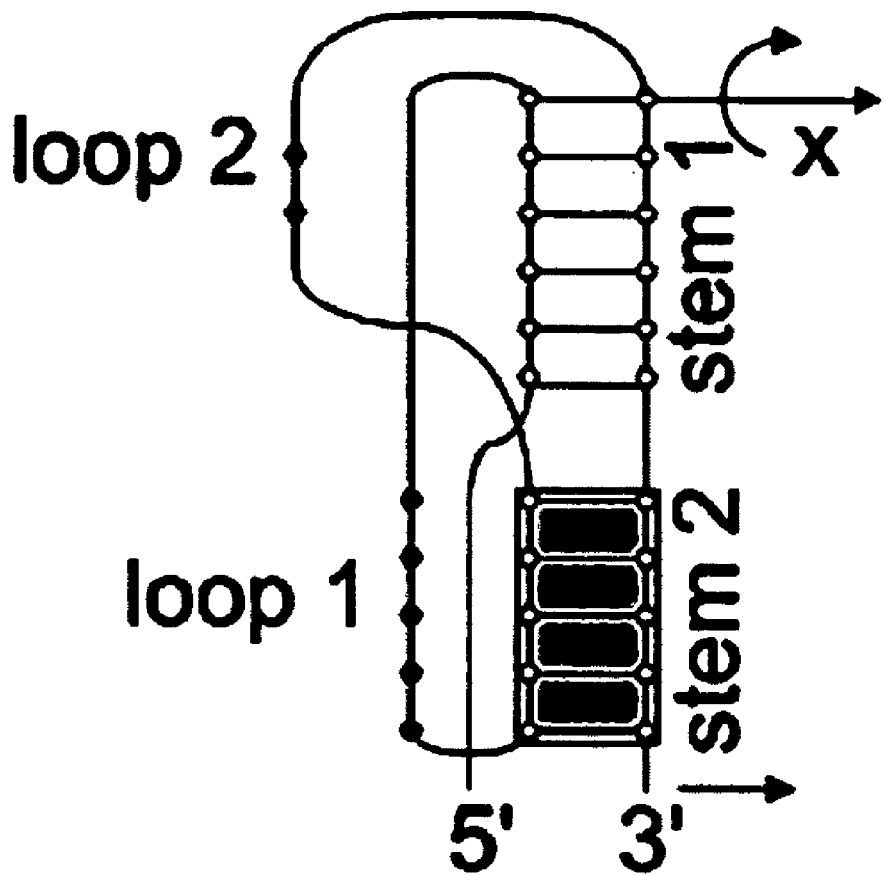
Figure 2A:
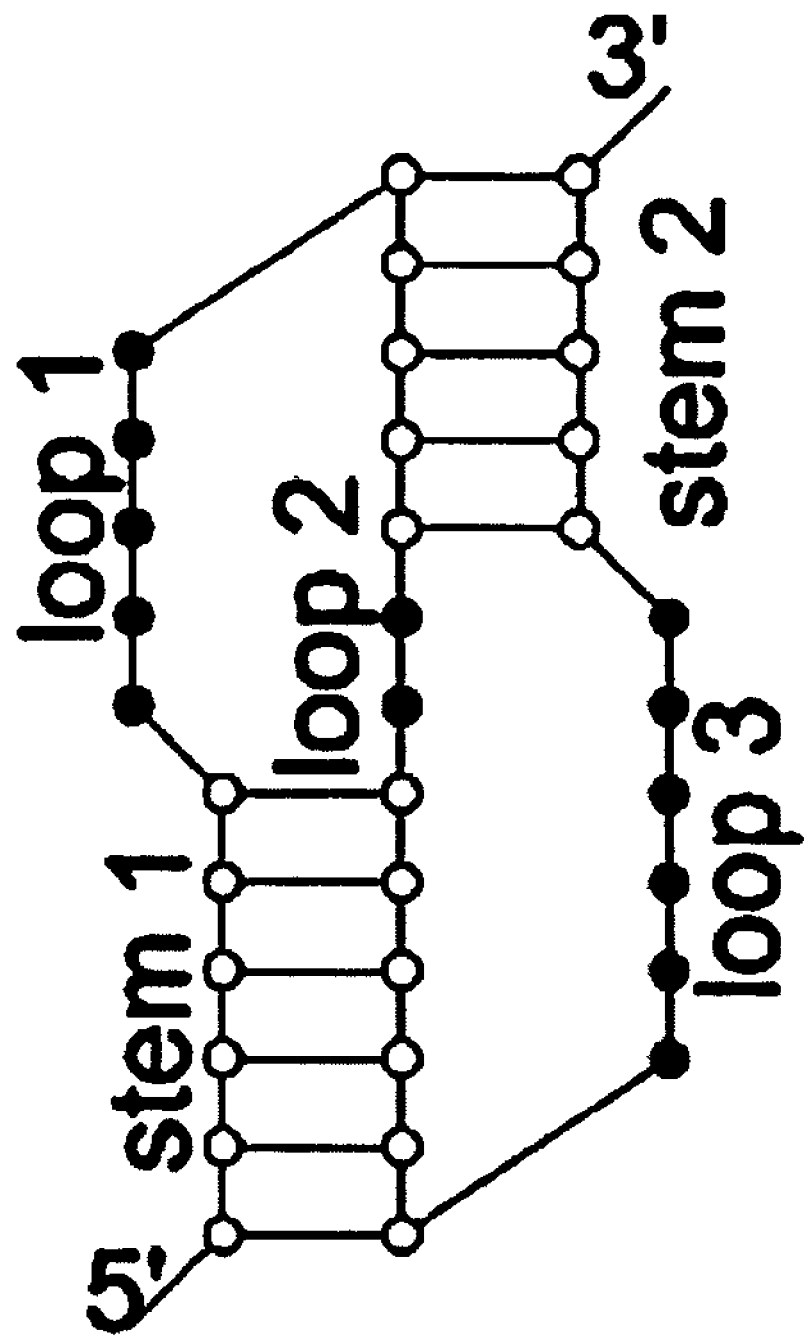
FIGS. 2a to 2d are schematic representations of H-type pseudoknots visualized according to the present invention.
Figure 2B:
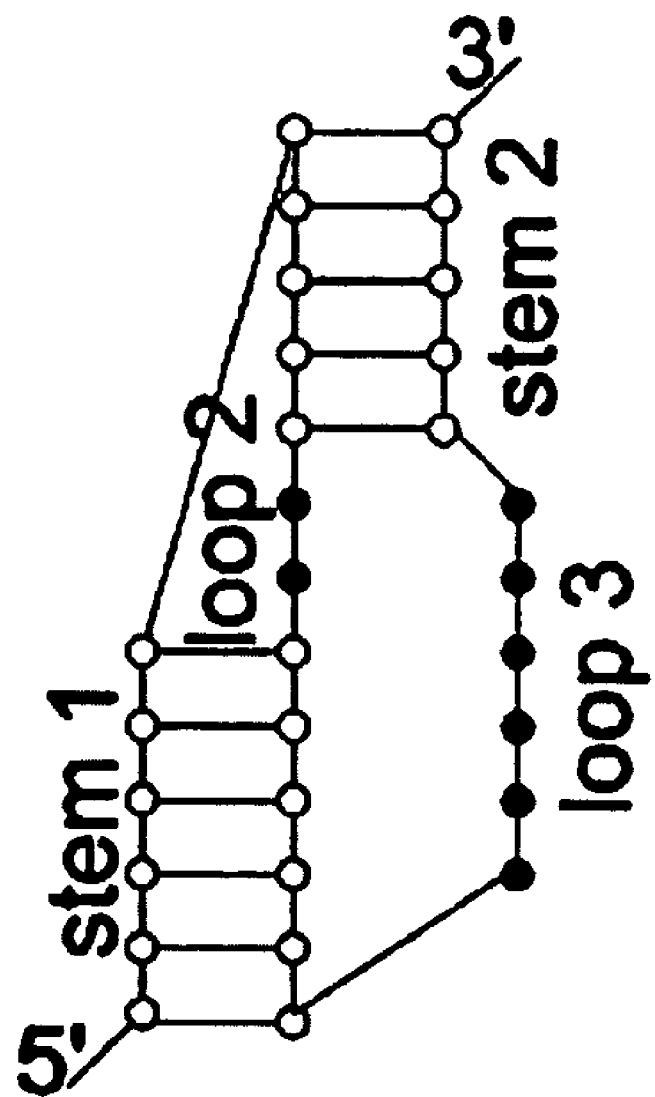
Figure 2C:
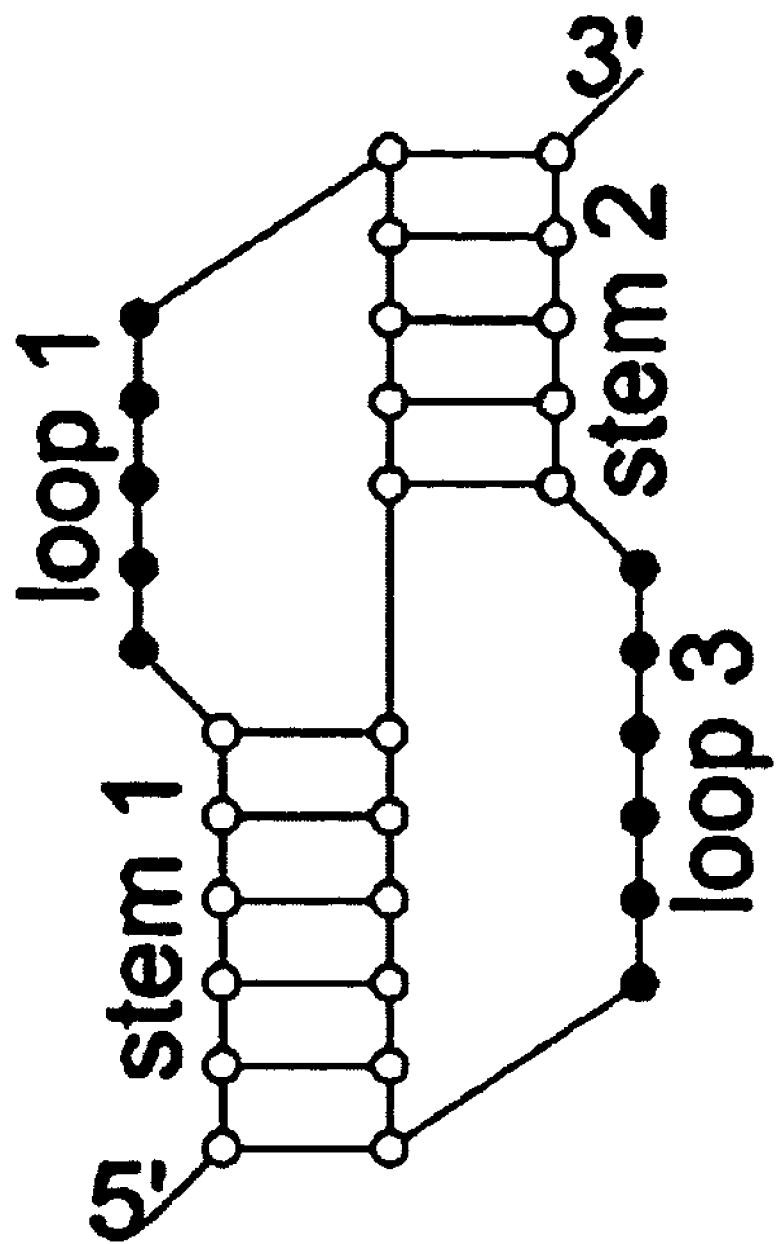
Figure 2D:
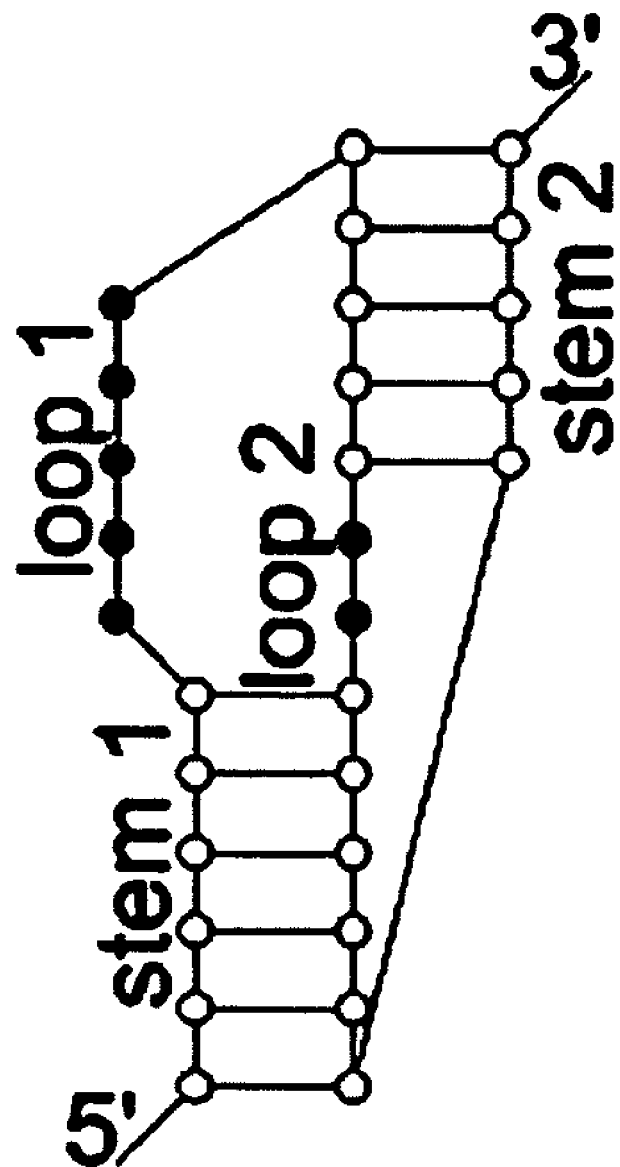

In particular, FIGS. 2a to 2d illustrate pseudoknot structures visualized according to the present invention. In detail, FIG. 2b is obtained by flipping the stem 2 of FIG. 1b with respect to the horizontal axis (x-axis) and translating it horizontally by the stem width. FIG. 2c is obtained by flipping the stem 2 of FIG. 1c with respect to the vertical axis (y-axis). FIG. 2d is obtained by flipping the stem 1 of FIG. 1d with respect to the horizontal axis (x-axis) and translating the stem 2 horizontally.

As shown in FIGS. 2a to 2d, H-type pseudoknot structures in accordance with the present invention do not contain the edge-crossing and do have similar shapes with exactly two inner cycles regardless of their types. In addition, H-type pseudoknot structures shown in FIGS. 2a to 2d make it easy to follow the RNA sequence direction from 5'-end to 3'-end. In these new structures, two stems of a pseudoknot are not stacked coaxially (on the same axis), but are represented adjacent to each other in parallel.

Figure 3A:
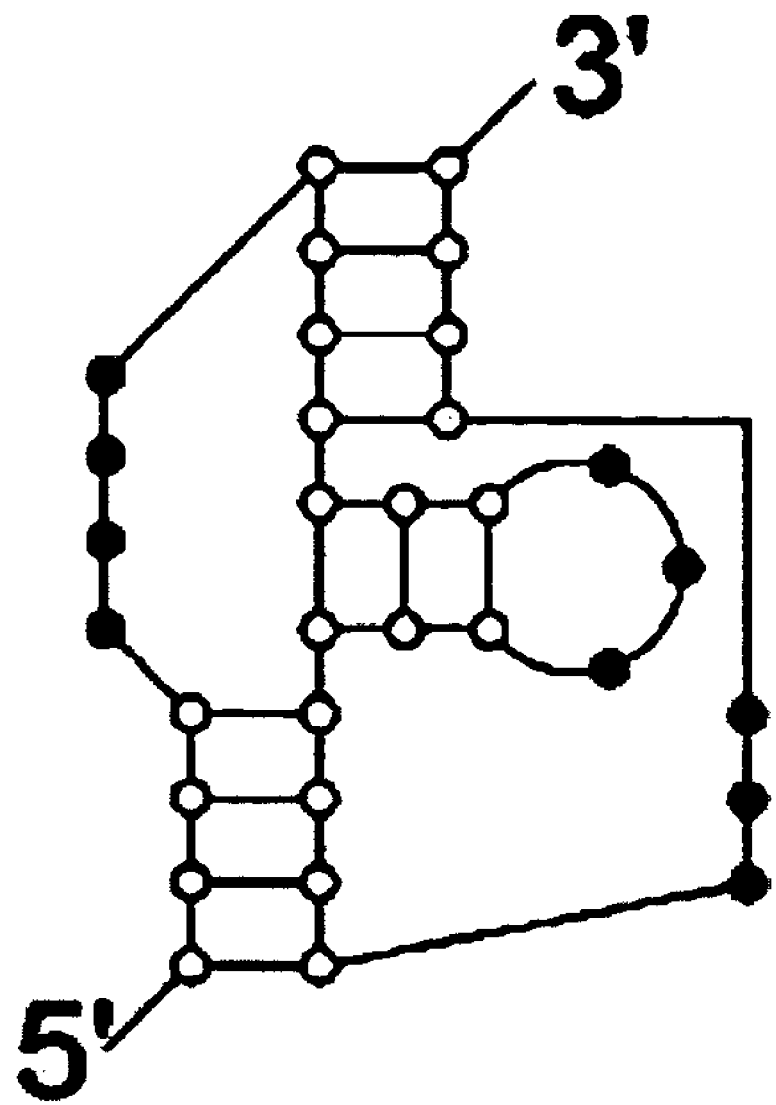
Figure 3B:
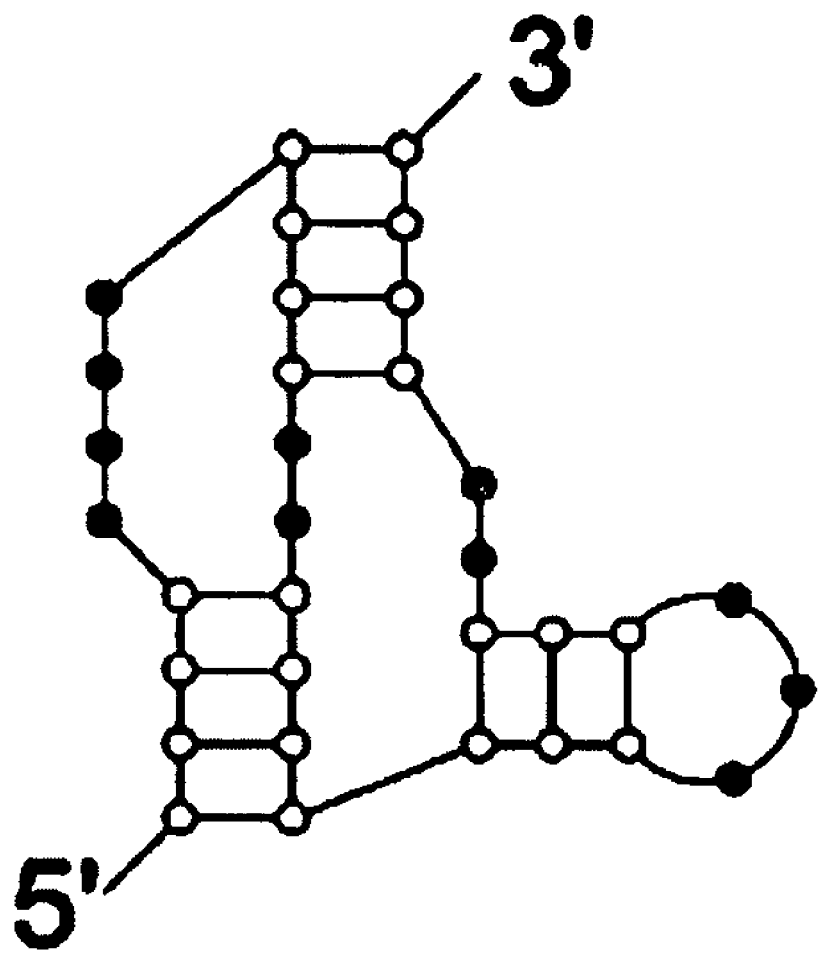
Figure 3C:
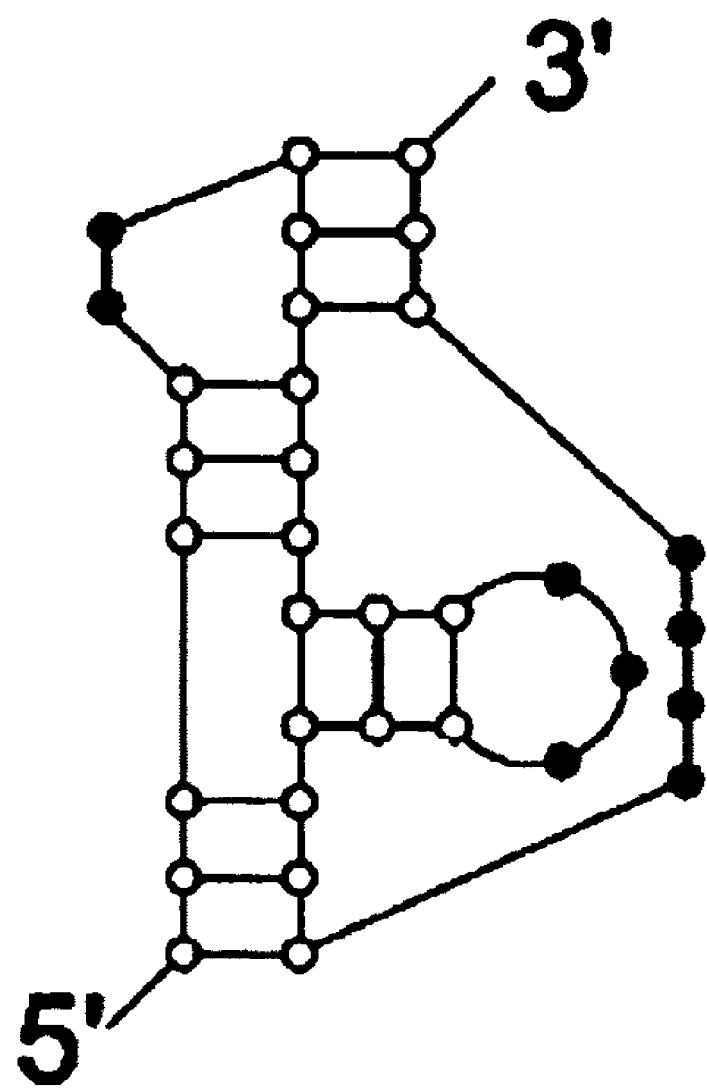
Figure 3D:
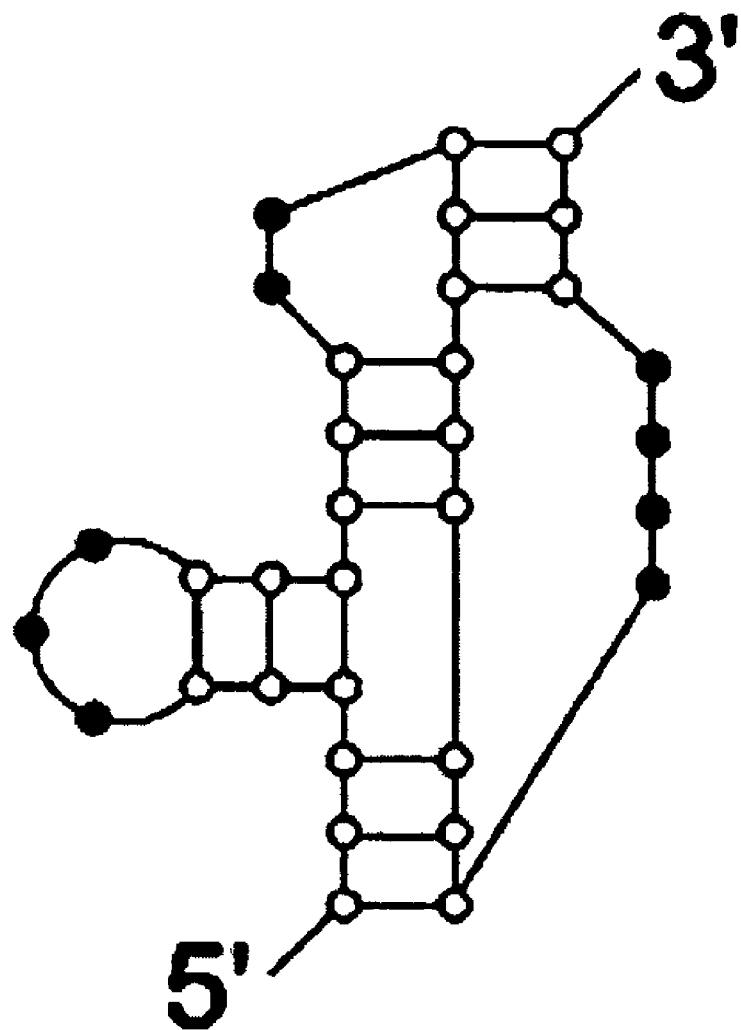
Figure 3E:
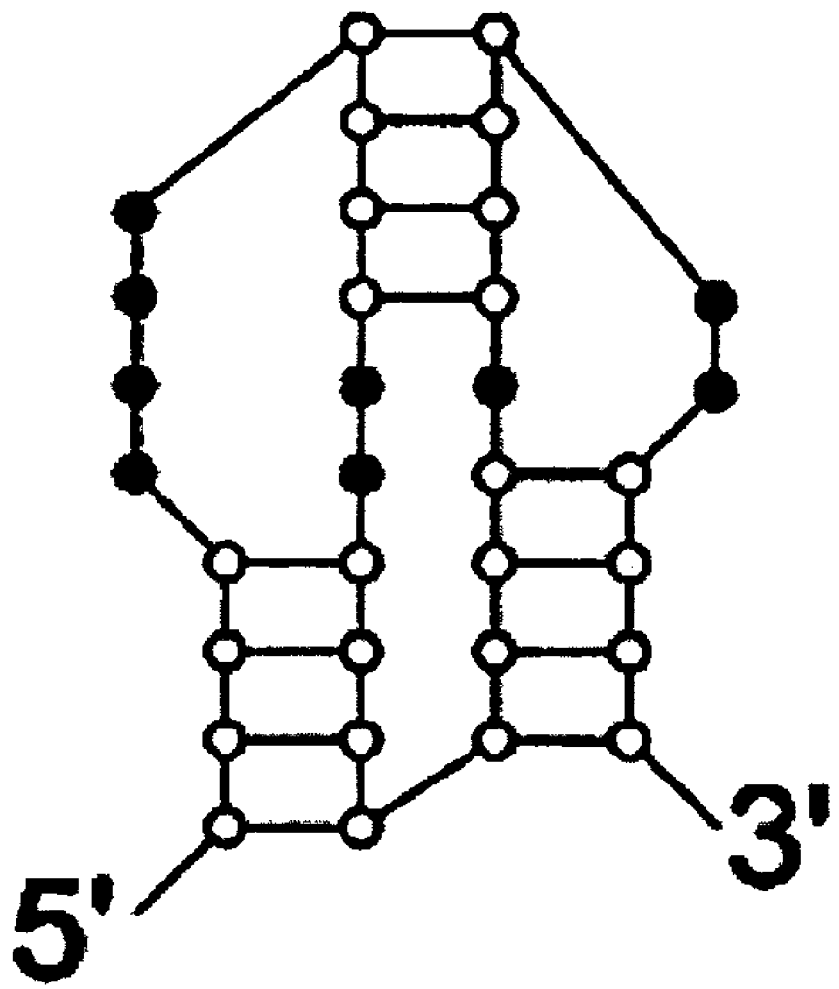

FIGS. 3a to 3e illustrate schematic representation of other types of pseudoknots except the H-type pseudoknot according to the present invention. Base pairing between a hairpin loop and a single stranded part outside the loop forms a H-type pseudoknot as mentioned above. Base pairing of a hairpin loop with another hairpin loop forms a HH type pseudoknot, while base pairing of a hairpin loop with a single stranded part of a bulge, or of an internal or multiple loop forms a HL type. The pseudoknot structures shown in FIGS. 3a to 3e have a similar shapes regardless of the type and make it easy to follow the RNA sequence from 5'-end to 3'-end. In addition, stems in the pseudoknot are represented adjacent to each other in parallel. Furthermore, FIG. 3a is an LL-type pseudoknot, FIGS. 3b and 3c are HL-type pseudoknots, FIG. 3d is an HH-type pseudoknot, and FIG. 3e is an HHH-type pseudoknot. In the above, H stands for a hairpin loop, L stands for one of a bulge loop, internal loop and multiple loop.

In the present invention, in order to visualize all types of pseudoknots by combining basic pseudoknot type structures, six basic pseudoknot types are determined, which are H-type as shown in FIGS. 1a to 1d, LL-type, HLout-type, HLin-type, HH-type, and HHH-type as shown in FIGS. 2a to 3e.

Table 1 below reports the classification of 236 pseudoknots, from which it can be noted that most of pseudoknots can be drawn in the form of a planar graph through the combination of basic pseudoknot types.

In Table 1 above, those designated with * include one or more basic type, respectively.

Now the visualization method of RNA pseudoknot structures of the present invention will be described in detail with reference to the FIG. 4 to FIG. 12.

Prior to description of the visualization method of the present invention, several terminologies will be defined first. In structure data, bracket pairs (for example '( )' and '[ ]') will represent base pairs, and ':' will represent bases of structure elements (loops) composed of single strands. The bracket pairs and their internal structure elements will be called stem-loops altogether. Also, a single hairpin loop-stem will be referred to as a simple loop-stem, and a stem-loop containing at least one other stem-loop will be referred to as a composite stem-loop. The composite stem-loop corresponds to an internal loop, a buldge loop, a multiple loop or a loop enclosing a pseudoknot.

According to the visualization method of the present invention, the stem-loop and the pseudoknot are identified respectively from the structure data and the simple stem-loop is computed before being environed by the composite stem-loop.

Figure 4:
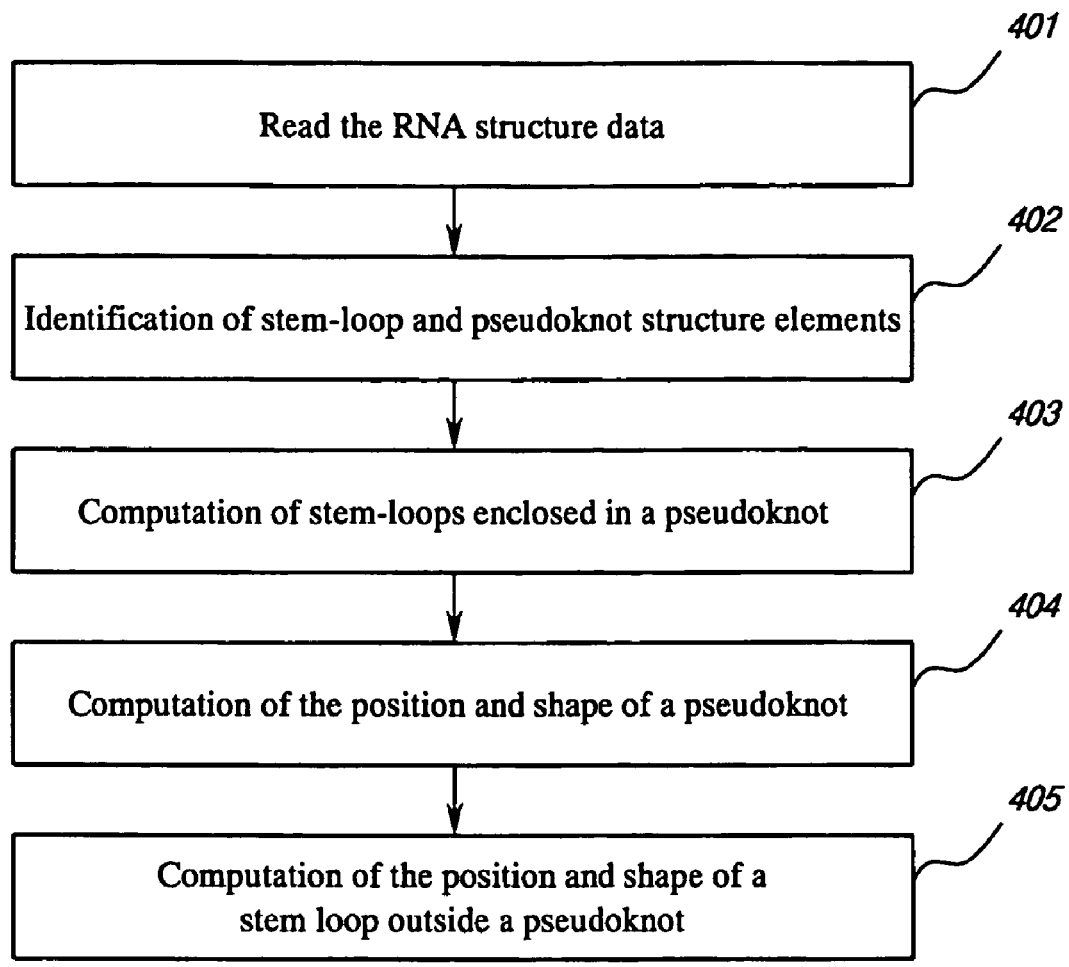
FIG. 4 is a flowchart for schematically illustrating a visualization method of RNA pseudoknot structures according to the present invention.

FIG. 4 is a flowchart schematically illustrating a visualization process of RNA pseudoknot structures according to the present invention. The visualization process of the invention is outlined as follows: stem-loops and pseudoknots are identified from the input structure data (step 402); the position and shape of a stem-loop enclosed in a pseudoknot is computed (403); the position and shape of a pseudoknot is computed (404); and the position and shape of a stem-loop outside a pseudoknot is computed (405). Hereinafter the visualization process will be described in detail with reference to the flowchart.

Stem-Loop and Pseudoknot Structure Elements Identification

Upon input of structure data in Step 401, stem-loops (including simple stem loops and composite stem loops) and pseudoknots are identified in Step 402.

Figure 5:
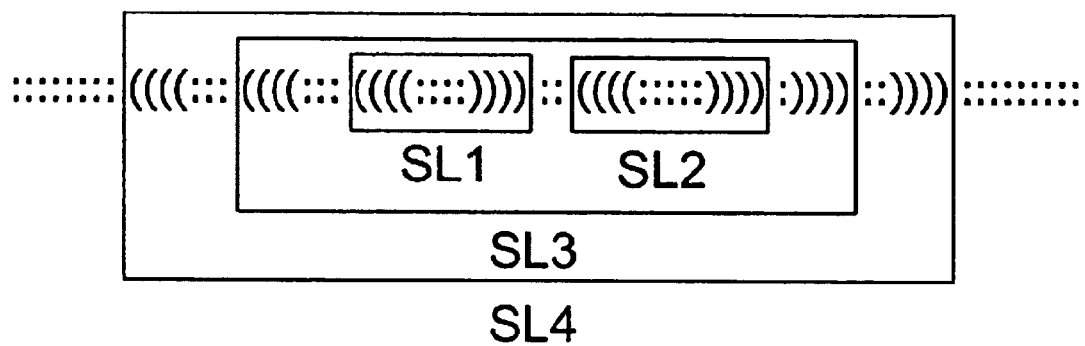
FIG. 5 is an example of data structure containing two simple stem-loops and two composite stem-loops according to the present invention.

Referring to an example of structure data as shown in FIG. 5, the structure data includes four stem-loops SL1 to SL4, in which SL1 and SL2 represent simple stem-loops that do not

TABLE 1

| Type | Pseudoknots | Number of occurrences | Ratio of occurrences |
|---|---|---|---|
| H | All others | 180 | 76.3% |
| LL | RSV, CGMMV_PKbulge, ORSV-S1-PKbulge1~3, PMMV-S_PKbulge, STMV_PKbulge, TMGMV_PKbulge, TMV_PKbulge, TMV-L_Pkbulge, Ec_RNaseP-P6*, HDV-It_ag* | 12 | 5.1% |
| $HL_{OUT}$ | AMV3, BBMV3*, BMV3*, BSMVbeta*, CCMV3*, CMV3*, LRSVbeta*, PSLVbeta*, satRPV*, BVDV_IRES, CSFV_IRES, BQCV_IRES-PKIII, CrPV_IRES-PKIII, DCV_IRES-PKIII, HiPV_IRES-PKIII, HDV-It_ag*, PSIV_IRES-PKIII, RhPV_IRES-PKIII, TrV_IRES-PKIII, Ec_23S-PKG12, Ec_RNaseP-P4, NGF-H1, NGF-L2, NGF-L6 | 24 | 10.2% |
| $HL_{IN}$ | BBMV3*, BMV3*, BSMVbeta*, CCMV3*, CMV3*, LRSVbeta*, Vp_PK2, PSLVbeta*, Pp_18S-PKE23-9/12, Ec_16S-PK570/866, Bp_PK2 | 11 | 4.7% |
| HH | HCV_IRES | 1 | 0.4% |
| HHH | HCV_229E, CoxB3, Ni_VS, satRPV*, Ec_RNaseP-P6*, Hs_SRP-pkn | 6 | 2.5% |
| Unclassified | Ec_alpha, HDV-It_g | 2 | 0.8% |
| total | | 236 | 100.0% | contain other stem-loops, SL3 represents a composite stem-loop environing SL1 and L2, and SL3 represents a composite stem-loop containing SL3.

Computation of Stem-Loops Enclosed in a Pseudoknot

In structure elements identified in Step 402 above, stem-loops enclosed in a pseudoknot are first computed in Step 403.

The stem-loops can be classified into simple stem-loops and composite stem-loops as determined above, in which the simple stem-loops are computed first, and then the composite stem-loops containing the simple stem-loops are computed.

1) Simple Stem-Loops

Figure 6:
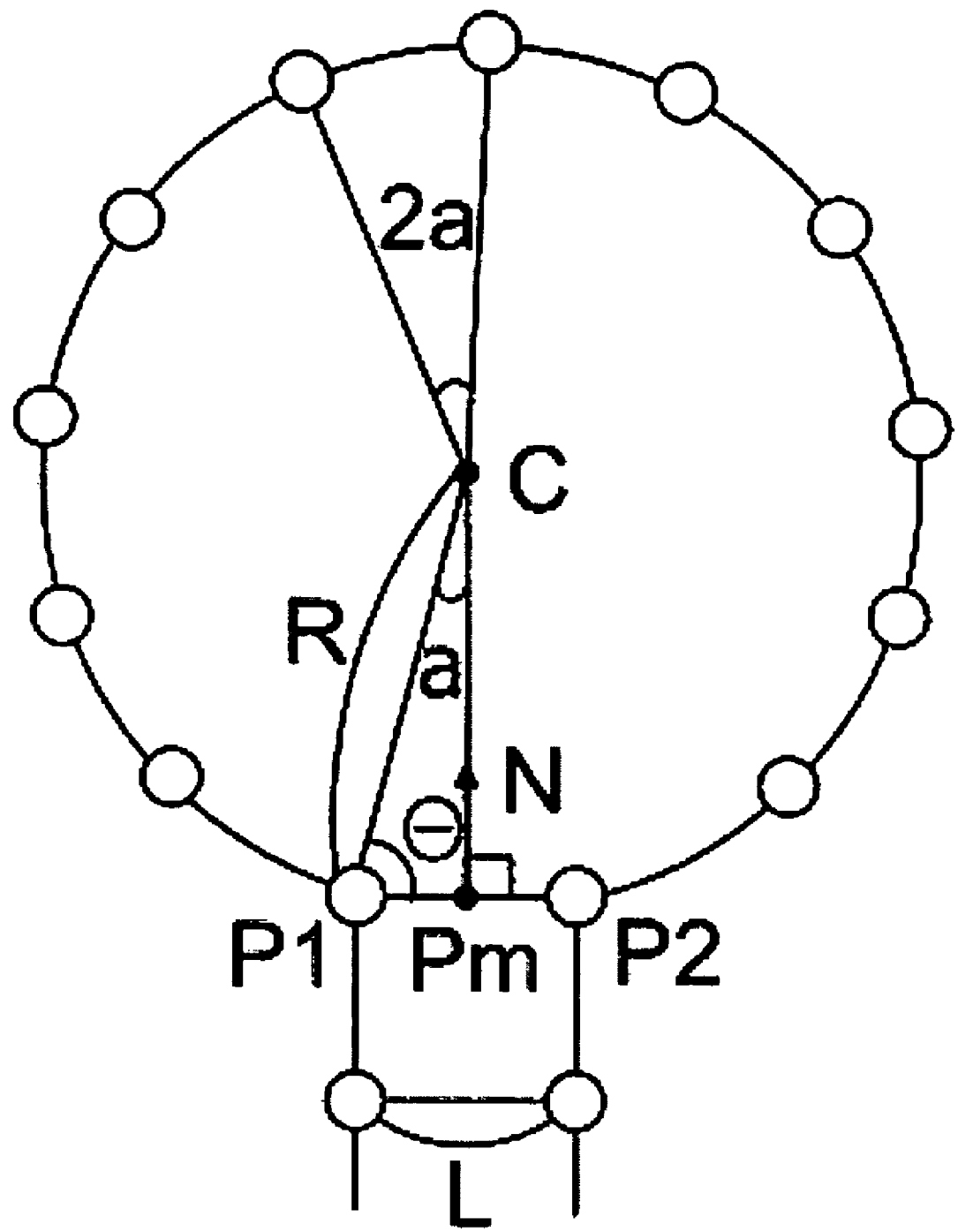
FIG. 6 is a schematic representation for illustrating the relationship of angle α, radius R, and loop center C in a simple stem-loop.

Base pairs of a stem in a simple stem-loop are stacked on the y-axis. In FIG. 6, L represents the distance between the base pairs of the stacked stem and the adjacent bases of a loop. The loop is arranged or drawn by an angle $2\alpha$ in a circle of a radius R from a loop center C as shown in FIG. 6.

If a natural number n represents "the number of bases in the loop region plus 2", the angle $\alpha$ and the radius R can be computed using Equations 1 and 2 below:

$$2\alpha \cdot n = 2\pi => \alpha = \frac{\pi}{n}, \text{ and} \qquad \text{Equation 1}$$

$$\sin(\alpha) = \frac{L/2}{R} => R = \frac{L}{2\sin(\alpha)}. \qquad \text{Equation 2}$$

In order to determine the loop center C, first the midpoint $P_m$ is computed from base pairs $P_1$ and $P_2$ connected to the loop as expressed in Equation 3:

$$\vec{P_m} = (x_m, y_m) = \frac{\vec{P_1} + \vec{P_2}}{2} = \left(\frac{x_1 + x_2}{2}, \frac{y_1 + y_2}{2}\right) \qquad \text{Equation 3}$$

In FIG. 6, if N is used as a unit vector which directs toward the loop center C from a point $P_m$, the vector N can be obtained by rotating the vector $P_2-P_1$ by 90° counterclockwise with respect to the midpoint $P_m$ and then by normalizing the rotated vector. The distanced between the loop center C and the midpoint $P_m$ is determined by Equation 4:

$$d = \|\vec{C} - \vec{P_m}\| = R\sin(\theta) = R\sin(\pi/2 - \alpha) \qquad \text{Equation 4.}$$

The position vector C representing the loop center C can be computed from the distance d, the vector N and the position vector $P_m$ as expressed in Equation 5:

$$\vec{C} = d \cdot \vec{N} + \vec{P_m} \qquad \text{Equation 5}$$

Using the loop radius R, the angle $\alpha$, the loop center C computed from structure data as above, bases on a single-stranded loop are located on the stacked stem according to a simple trigonometric functions.

With the afore-described process, it is possible to compute the shape and position of the simple stem-loops identified from the structure data.

2) Composite Stem-Loops

Figure 7:
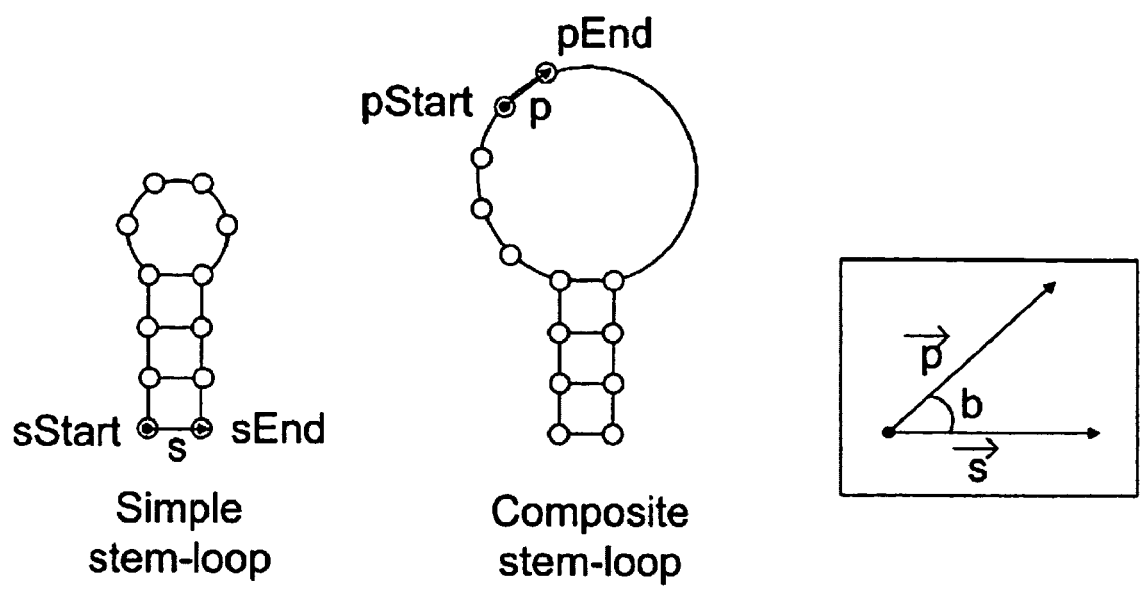
FIG. 7 is a schematic representation for illustrating start-end vectors of simple and composite stem-loops.

FIG. 7 illustrates a computation process of composite stem-loops. Consider a composite stem-loop pSL containing a simple stem-loop sSL in the FIG. 7. Then it is assumed that sStart represents the position of the first base of sSL before being connected to the composite stem-loop pSL; sEnd represents the position of the last base of the simple stem-loop sSL before being connected to the simple stem-loop pSL; pstart represents the position at which the first base of the simple stem-loop sSL is to be located in the composite stem-loop pSL; and pEnd represents the position at which the last base of the simple stem-loop sSL is to be located in the composite stem-loop pSL. Assuming that s is used as the unit vector indicating the direction of sEnd-pStart of the afore-computed simple stem-loop sSL and vector p as the unit vector indicating the direction of pEnd-pStart, the angle b between orientations of the simple stem-loop sSL before and after being connected to the composite stem-loop pSL is computed as Equation 6 below:

$$\vec{s} = \frac{\overrightarrow{sEnd} - \overrightarrow{sStart}}{\|\overrightarrow{sEnd} - \overrightarrow{sStart}\|}$$

$$\vec{p} = \frac{\overrightarrow{pEnd} - \overrightarrow{pStart}}{\|\overrightarrow{pEnd} - \overrightarrow{pStart}\|}$$

$$b = \cos^{-1}(\vec{p} \cdot \vec{s}). \qquad \text{Equation 6}$$

Therefore, the simple stem-loop sSL can be inserted into the composite stem-loop by rotating the simple stem-loop, which is to be connected to the composite stem-loop computed in the previous step, by the angle b and then translating the rotated simple stem-loop using the vector move as in the following Equation 9 below:

$$\overrightarrow{move} = \overrightarrow{pStart} - \overrightarrow{sStart} \qquad \text{Equation 9.}$$

Other base pairs of a stem in the loop region of a composite stem-loop are located in the same way as a simple stem-loop.

Figure 8:
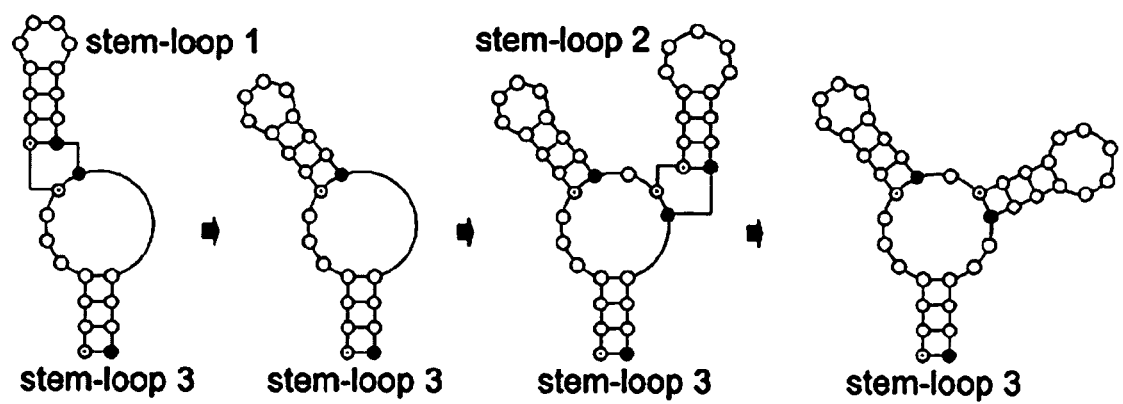
FIG. 8 is an example view for illustrating the insertion of two simple stem-loops into a composite stem-loop by rotating and/or translating the simple stem-loops according to the present invention.

FIG. 8 illustrates a stepwise process of inserting a stem-loop 1 and a stem-loop 2 into a stem-loop 3 by rotation and translation afterward.

The following algorithm summarizes the process of computing and visualizing the position and shape of a stem-loop above:

--- for each stem-loop do     {start with the innermost stem-loop}
    1. Compute the position of the stem in the stem-loop.
    2. Compute the radius and center of the loop in the stem-loop.
    3. Compute the position of each base of the loop.
    4. If the stem-loop has an enclosed stem-loop or pseudoknot
    5.    Insert it by rotating it and moving it
end for

---

Computation of the Position and Shape of a Pseudoknot

The present invention divides a pseudoknot into several parts to simplify the visualization or drawing process of a pseudoknot.

Figure 9:
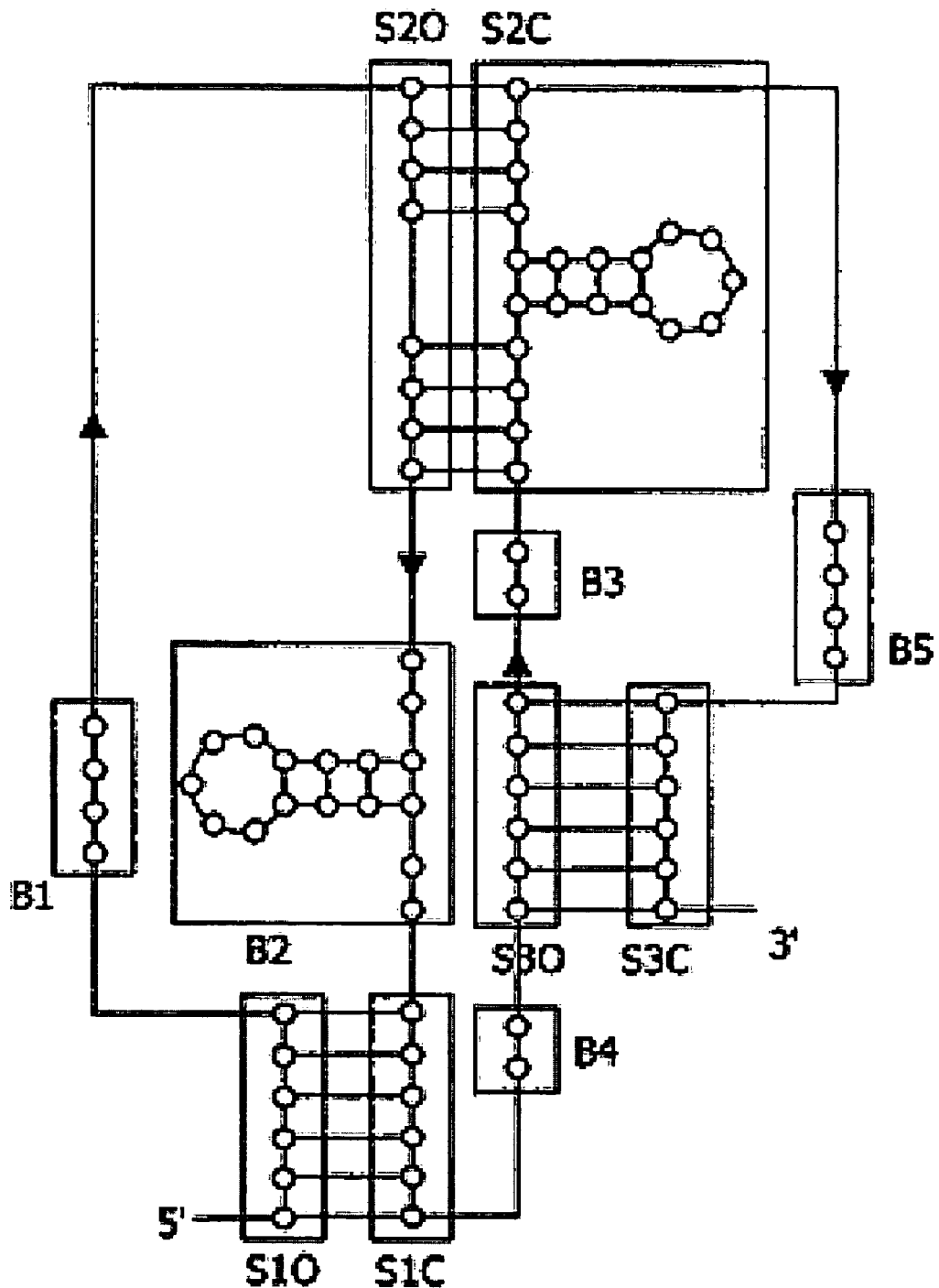
FIG. 9 is a schematic representation of a hypothetical pseudoknot containing all basic pseudoknot types.
Figure 10:
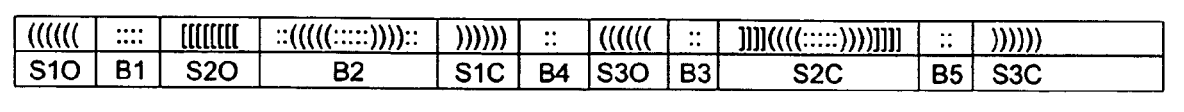

FIG. 9 illustrates a hypothetical pseudoknot containing all structure elements of all pseudoknot types, and FIG. 10 illustrates a structure data of the pseudoknot shown in FIG. 9.

That is, the structure elements in FIGS. 9 and 10 contain all the structure elements of 6 basic pseudoknot types described as above.

Referring to FIG. 9, an RNA pseudoknot includes a part or the entire of the following elements such as a first stem S1 with the first base being connected to 5'-end, a second stem S2 with its first base being connected to the last base of the first stem S1, a third stem S3 with its first base being connected to the last base pair of the second stem S2 and its last base being connected to 3'-end and first to fifth internal structure elements B1 to B5.

The first to fifth internal structure elements B1 to B5 are either unpaired bases located between the first to third stems S1 to S3 or stem-loops, and defined as follows:

The first internal structure element B1 is a structure element between the opening part of the first stem S1O and the opening part of the second stem S2O of the pseudoknot, the second internal structure element B2 is a structure element between the opening part of the second stem S2O and the closing part of the first stem S1C of the pseudoknot, the third internal structure element B3 is a structure element between the closing part of the second stem S2C and the opening part of the third stem S3O of the pseudoknot, the fourth internal structure element B4 is a structure element between the closing part of the first stem S1C and the opening part of the third stem S3O of the pseudoknot, and the fifth internal structure element B5 is a structure element between the closing part of the second stem S2C and the closing part of the third stem S3C of the pseudoknot.

Depending on the type of a pseudoknot, it may or may not contain more than one parts of the internal structure elements B1 to B5. For example, the third internal structure element B3, the third stem S3 and the fifth internal structure element B5 are missing in a non-HHH type pseudoknot.

Among the structure elements of a pseudoknots, base pairs of a stem are located along the vertical axis (y-axis), and each pair of bases have the same y coordinates in the local coordinate system of the stem.

After the above classification, a pseudoknot is visualized or drawn by computing the position and shape of each part and then processing and inserting the each part into the pseudoknot as follows:

1. Stem-loops located in the opening part of the first stem S1O, the first internal structure element B1 and the opening part of the third stem S3O are rotated by 90° counterclockwise and inserted into the pseudoknot.

Figure 11:
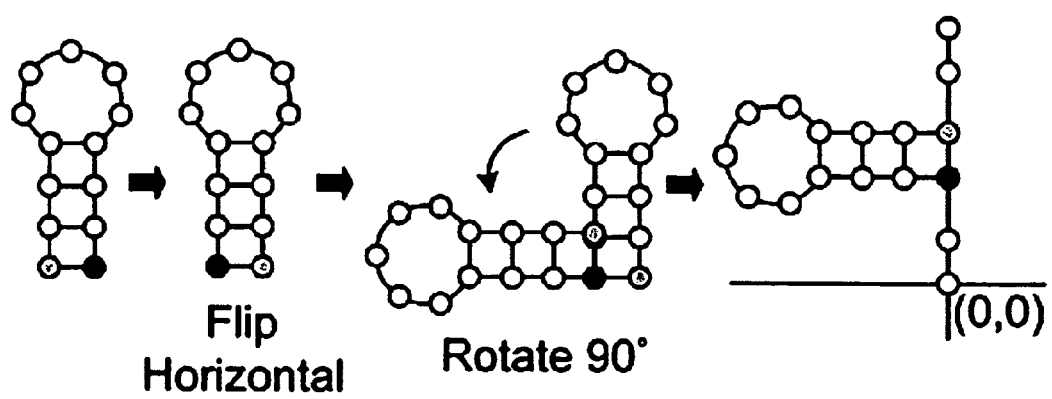
FIG. 11 is an example view for illustrating the insertion of a simple stem-loop into a pseudoknot by flipping and rotating the simple stem-loop according to the present invention.

2. Stem-loops in the opening part of the second stem S2O and the second internal structure element B2 are horizontally flipped, rotated by 90° counterclockwise, and then inserted into the pseudoknot. FIG. 11 illustrates this procedure.

3. Stem-loops in the closing part of the first stem S1C, the fifth internal structure element B5 and the closing part S3C of the third stem are rotated by 90° clockwise and then inserted into the pseudoknot.

4. Stem-loops in the third internal structure elements B3, the fourth internal structure element B4 and the closing part of the second stem S2C are flipped horizontally, rotated by 90° clockwise, and the inserted into the pseudoknot.

When a stem-loop is inserted into the step part such as the opening part of the first stem S1O, the closing part of the first stem S1C, the opening part of the second stem S2O, the closing part of the second stem S2C, the opening part of the third stem S3O and the closing part of the third stem S3C, a pair of bases in either of the opening part or of the closing part of the stem are adjusted in their position to have the same y coordinate.

Figure 12:
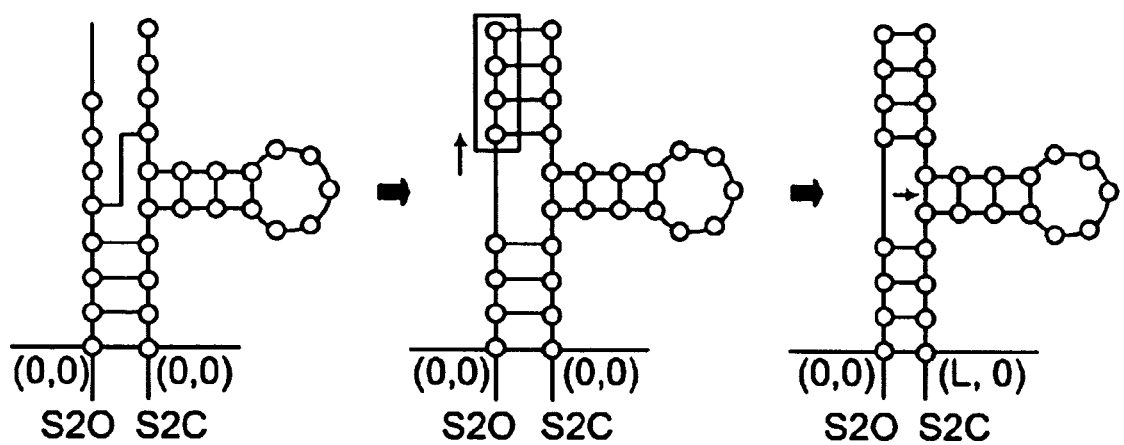
FIG. 12 is an example view for illustrating the position adjustment of bases of a pseudoknot into which a simple stem-loop is inserted according to the present invention.

For example, referring to FIG. 12 a stem-loop is inserted into the closing part of the second stem S2C, and the y coordinates of a pair of bases of the opening part of the second stem S2O are adjusted so that two bases consisting a pair of the second stem have the same y coordinate to clearly visualize or draw the stem-loop.

The following algorithm illustrates an actual example of the algorithm for visualizing or drawing the hypothetical pseudoknot shown in FIG. 9 according to the afore-described visualization process of a pseudoknot:

---

```
Put S1O upright.
Put B1 above S1O with the following adjustments.
    If B2 or S2O contains a stem-loop
        Shift B1 left by the size of the stem-loop
    Else
        Shift B1 left by L (the basis distance between a pair of bases)
Put S1C to the right of S1O.
Put B2 above S1C, and S2O above B2.
Put S2C to the right of S2O.
Put B3 below S2C.
If the pseudoknot is not of HHH type
Shift B3 right by L.
Else
    If S1C or S3O contains a stem-loop
        Shift B3 right by the size of the stem-loop.
    Put S3O below B3.
    Put B4 below S3O.
    Put S3C to the right of S3O.
    Put B5 above S3C with the following adjustments.
        If S2C or B3 contains a stem-loop
            Shift B5 right by the size of the stem-loop.
        Else
            Shift B5 right by L.
```

---

Upon visualization of a pseudoknot by computing its position and shape, a stem loop outside the pseudoknot is visualized by computing its position and shape in the same way as above, and then inserted together with the pseudoknot into a secondary structure of a corresponding RNA so that an RNA pseudoknot structure is visualized in Step 405.

The afore-described visualization method of an RNA pseudoknot may be programmed in Microsoft Visual C#, and is executable within a web browser on any PC with Windows 2000/XP/Me/98/NT4.0 as its operating system.

The visualization method of at least one RNA pseudoknot takes as input an RNA sequence with its structure data in bracket view, which is widely used for representing pseudoknots. The bracket view can describe pseudoknots and secondary structures in one of two styles reported in the following two algorithms.

---

```
Bracket view I
# <RNA name>           //optional; if this line may be omitted
<base sequence>
<matching parentheses and brackets>
<starting base number> //optional; if this is omitted, the starting
                         number is 1 by default.
# TYMV
UUAGCUCGCCAGUUAGCGAGGUCUGUCCCCACACGACAGAUAAUCGGGUG
CAACUCCCGCCCCUUUUCCGAGGGUCAUCGGAACCA
::::(((((:::::::))))):(((((:::::::)))))::::(((::
:::::))))(((:::[[[[[)))::::]]]]]:::
1
```
---

```
Bracket view II
# <RNA name> //optional; if this line may be omitted
<base sequence> alternates with
<matching parentheses and brackets>
<starting base number> //optional; if this is omitted, the starting
                          number is 1 by default.
# TYMV
UUAGCUCGCCAGUUAGCGAGGUCUGUCCCCACACGACAGAUAAUCGGGUG
::::(((((((:::::))))):(((((((:::::::))))))::::((((::
CAACUCCCGCCCCUUUUCCGAGGGUCAUCGGAACCA
:::::))))(((:::[[[[[)))::::]]]]]:::
1
```

Figure 13:
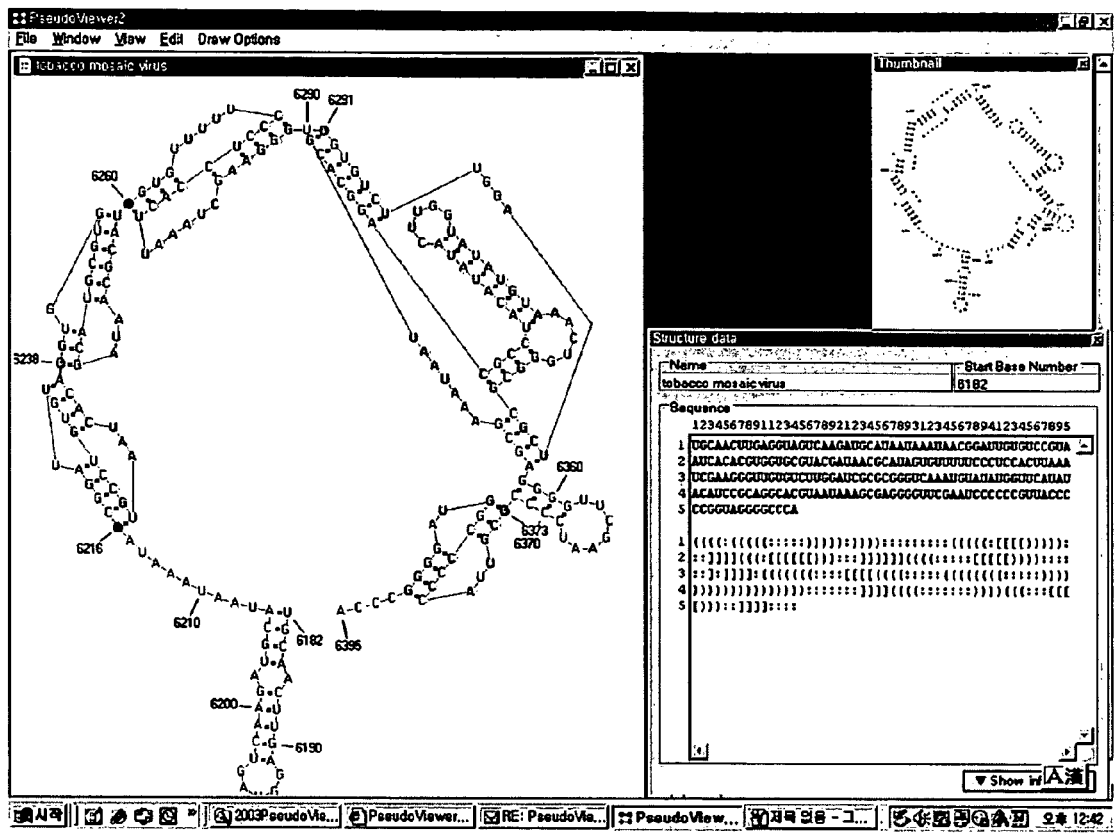
FIG. 13 illustrates a computer interface display which is obtained through the visualization method of RNA pseudoknots according to the present invention.

The visualization method of a pseudoknot of the present invention can produce a structure drawing as an output. In the standard view, RNA pseudoknots and secondary structures are displayed in the specified form of symbols between bases and paired bases as shown in FIG. 13.

The structure drawing displays the structure in the form of a backbone where loops are rearranged polygons and helices of line segments. A structure data window in bracket view is also respectively provided to display any input base sequence and its corresponding structure elements thereby depicting the structure drawing of the base sequence.

Figure 14:
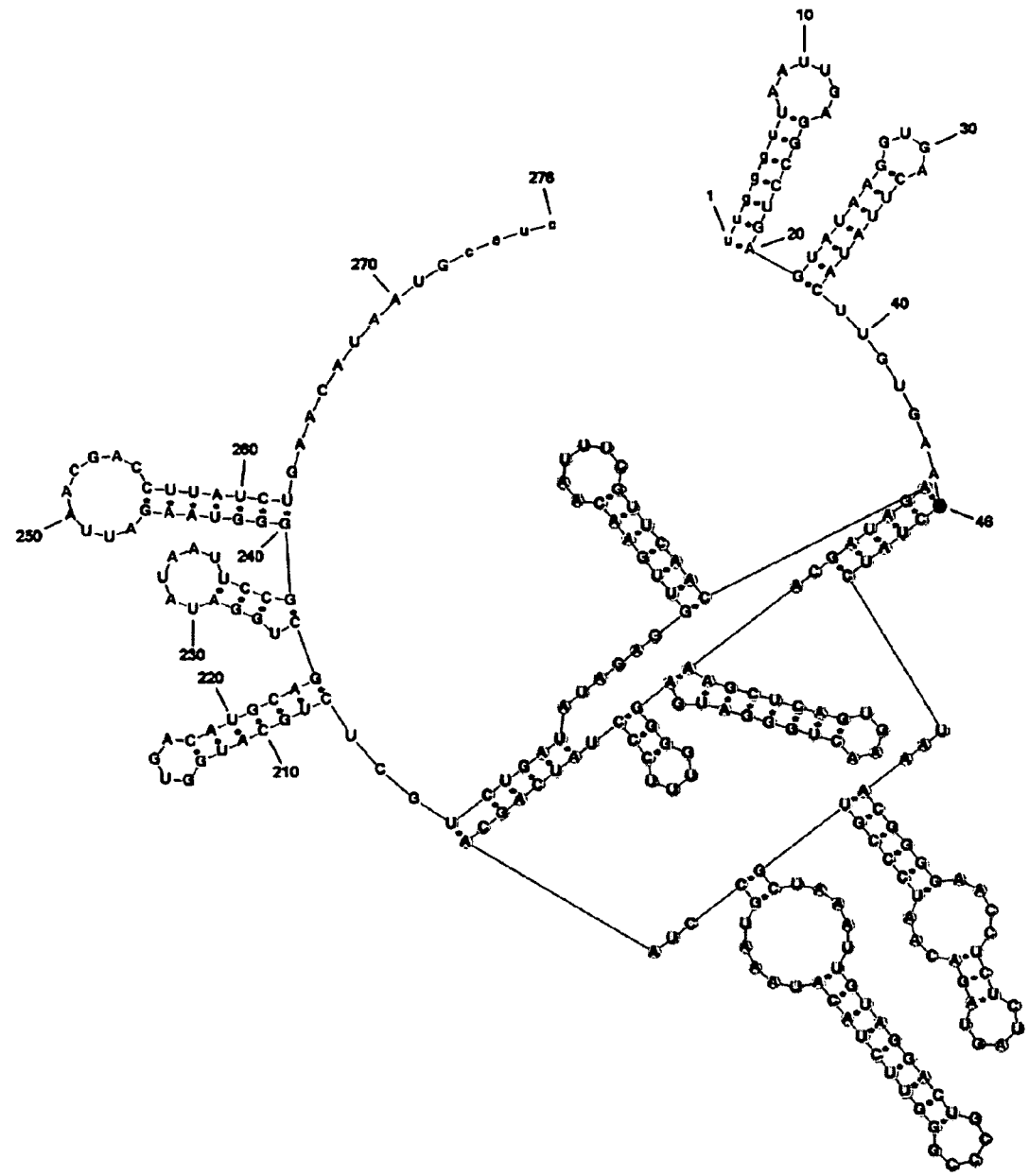
FIG. 14 illustrates the structure of a td group intron of a bacteriophage T4 drawn according to the present invention.

FIG. 14 illustrates the structure drawing of the td group I intron of bacteriophage T4 visualized according to the present invention. Although it is a very complex structure with a non-H type pseudoknot, the visualization method of the present invention represents the structure in the form of a planar graph without edge crossings. The starting base of each pseudoknot is shown in its own background color and with their base number different from those of other structure elements and thus easily distinguished therefrom. Thus, structure drawings generated according to the invention are displayed more aesthetically and clearly over conventional manual drawings of pseudoknots.

For the comparison of actual running times, test was performed on RNAs with H-type pseudoknots such as tobacco mosaic, satellite tobacco mecrosis virus 1, *E. coli* tmRNA, satellite tobacco virus, odontoglossum ringpot virus and *Cyanophora paradoxa* cyanelle tmRNA. The running times for visualizing the test cases on a Pentium IV 1.5 GHz processor were 14 ms, 30 ms, 30 ms, 92 ms, 108 ms and 145 ms, respectively, which are proportional to the numbers of pseudoknots and bases. It can be understood that the observer rarely recognizes the running times for visualizing several RNA molecular structures and thus the process is executed much more rapidly compared to the conventional manual process.

Table 2 below compares results of the above test.

TABLE 2

| RNA | # bases | # pseudoknots | time of PSEUDOVIEWER1 | time of PSEUDOVIEWER2 |
| --- | --- | --- | --- | --- |
| tobacco mosaic virus | 214 | 4 | 15 ms | <1 ms |
| satellite tobacco necrosis virus 1 | 252 | 4 | 31 ms | <1 ms |
| *E. coli* tmRNA | 363 | 4 | 31 ms | <1 ms |
| satellite tobacco mosaic virus | 421 | 7 | 93 ms | <1 ms |
| *Odontoglossum* ringspot virus | 419 | 8 | 109 ms | <1 ms |
| *Cyanophora paradoxa cyanelle* tmRNA | 291 | 1 | 146 ms | <1 ms |

The present invention can automatically and efficiently visualize RNA pseudoknot structures containing inner cycles and outer cycles formed between pseudoknots and other structure elements without manual operation. The RNA pseudoknot structures can be visualized in the form of a planar graph without edge crossing so that the observer can understand the corresponding structures more easily. Furthermore, the visualization method of the invention can be realized with a web-based program and thus is outstandingly effective for easy use.

Moreover, the present invention has an excellent effect that all types of pseudoknot structures regardless of their types can be automatically visualized in the form of a planar graph without edge crossing.

$$\vec{P_m} = (x_m, y_m) = \frac{\vec{P_1} + \vec{P_2}}{2} = \left(\frac{x_1 + x_2}{2}, \frac{y_1 + y_2}{2}\right)$$

wherein $x_1$, $x_2$, $y_1$ and $y_2$ are coordinates of the last base pair $p_1$ and $p_2$-, d is the distance from the midpoint $P_m$ to the loop center C, that is, $\|\vec{C} - \vec{P_m}\| = R\sin(\theta) = R\sin(\pi/2 - \alpha)$, and N is the unit vector directed toward the loop center from the midpoint $P_m$;

arranging the stem-loop at an angle $2\alpha$ on a circle of a radius R from a loop center C with the processor;

computing vectors s and p as in an equation below with the processor, if simple stem-loops are identified in the iden-

---

---

What is claimed is:

1. A computer implemented method for visualization of RNA pseudoknot structures, the method comprising:

reading structure data in bracket view with a computer input device;

identifying simple stem-loops, composite stem-loops and pseudoknots enclosed in bracket pairs from the structure data with a processor, wherein the simple stem-loops are single hairpin stem-loops not containing other stem-loops and the composite stem-loops are stem-loops containing one or more other stem-loops;

first stacking base pairs of a stem-loop on a vertical axis or y-axis to have the same y coordinate;

computing a loop center C, a loop radius R and a base-to-base angle of loop α according to equations below:

$$2\alpha \cdot n = 2\pi \Rightarrow \alpha = \frac{\pi}{n},$$

$$\sin(\alpha) = \frac{L/2}{R} \Rightarrow R = \frac{L}{2\sin(\alpha)}, \text{ and}$$

$$\vec{C} = d \cdot \vec{N} + \vec{P_m},$$

wherein n is the number of bases in the loop plus 2, L is the distance between a base pair and an adjacent base, $\vec{P_m}$ is the midpoint vector of the last base pair $p_1$ and $p_2$ of the stem, tifying step, using sStart that is the position of the first base of a stem-loop before being connected to a composite stem-loop, sEnd that is the position of the last base of the simple-loop before being connected to the composite stem-loop, pStart that is the position of the first base of the simple stem-loop after being connected to the composite stem-loop and pEnd that is the position of the last base of the simple stem-loop after being connected to the composite stem-loop:

$$\vec{s} = \frac{\overrightarrow{sEnd} - \overrightarrow{sStart}}{\|\overrightarrow{sEnd} - \overrightarrow{sStart}\|}, \text{ and}$$

$$\vec{p} = \frac{\overrightarrow{pEnd} - \overrightarrow{pStart}}{\|\overrightarrow{pEnd} - \overrightarrow{pStart}\|},$$

computing an angle b with the processor, if simple stem-loops are identified in the identifying step, according to $b = \cos^{-1}(\vec{p} \cdot \vec{s})$ using the computed vectors s and p, rotating the stem-loop with the processor, which is to be contained in other composite stem-loop, for the angle b; and translating and inserting the rotated stem-loop into the corresponding composite stem-loop with the processor, if simple stem-loops are identified in the identifying step;

second computing the position and shape of the pseudoknot containing the calculated stem-loop with the processor to visualize the pseudoknot;

third computing the position and shape of a stem-loop outside the computed pseudoknot with the processor;

connecting the visualized stem-loops to the pseudoknot with the processor to complete an RNA pseudoknot structure drawing; and displaying the RNA pseudoknot structure drawing on a computer interface display;

wherein the visualized stem-loops are rotated and inserted or connected into or to the pseudoknot without forming edge-cross in the RNA pseudoknot structure drawing.

2. The computer implemented method for visualization of RNA pseudoknot structures according to claim 1, wherein the second computation step comprises:

classifying the identified pseudoknot into stems and internal structure elements located between the stems with the processor;

vertically arranging the stems with the processor so that each base pair has the same y coordinate;

computing the position and shape of each internal structure element with the processor to visualize the internal structure element; and inserting the visualized internal structure element into a designated stem or between designated stems with the processor.

3. The computer implemented method for visualization of RNA pseudoknot structures according to claim 2, wherein the classification step classifies the pseudoknot into at least one selected from group including: a first stem with the first base being connected to 5'-end, a second stem with the first base being connected to the last base of the first stem, a third stem with the first base being connected to the last base pair of the second stem and the last base being connected to 3'-end and first to fifth internal structure elements which are either unpaired bases located between the first to third stems or stem-loops.

4. The computer implemented method for visualization of RNA pseudoknot structures according to claim 3, wherein the first internal structure element is a structure element between an opening part of the first stem and an opening part of the second stem of the pseudoknot, wherein the second internal structure element is a structure element between an opening part of the second stem and a closing part of the first stem of the pseudoknot, wherein the third internal structure element is a structure element between a closing part of the second stem and an opening part of the third stem of the pseudoknot, wherein the fourth internal structure element is a structure element between a closing part of the first stem and an opening part of the third stem of the pseudoknot, and wherein the fifth internal structure element is a structure element between a closing part of the second stem and a closing part of the third stem of the pseudoknot.

5. The computer implemented method for visualization of RNA pseudoknot structures according to claim 2, wherein the insertion step comprises:

rotating stem-loops located in the opening part of the first stem, the first internal structure element and the opening part of the third stem 90° counterclockwise before insertion with the processor;

horizontally flipping stem-loops in the opening part of the second stem and the second internal structure element and rotating the same 90° counterclockwise before insertion with the processor;

rotating stem-loops in the closing part of the first stem, the fifth internal structure element and the closing part of the third stem 90° clockwise before insertion with the processor; and horizontally flipping stem-loops in the third internal structure elements, the fourth internal structure element and the closing part of the second stem and rotating the same 90° clockwise before insertion with the processor.

6. The computer implemented method for visualization of RNA pseudoknot structures according to claim 2, further comprising: adjusting positions of bases in either the opening part or the closing part of the inserted stem so that a pair of bases have the same y coordinate with the processor.

* * * * *

UNITED STATES PATENT AND TRADEMARK OFFICE
CERTIFICATE OF CORRECTION

| | | |
|---|---|---|
| PATENT NO. | : 7,974,786 B2 | |
| APPLICATION NO. | : 10/852872 | |
| DATED | : July 5, 2011 | |
| INVENTOR(S) | : Kyungsook Han and Yan A. Byun | |

It is certified that error appears in the above-identified patent and that said Letters Patent is hereby corrected as shown below:

Column 14, line 7, claim 1, "$p_2$-" should be --$p_2$--.

Signed and Sealed this
Eleventh Day of October, 2011

David J. Kappos
*Director of the United States Patent and Trademark Office*

SEQUENCE LISTING

<160> NUMBER OF SEQ ID NOS: 1

<210> SEQ ID NO 1
<211> LENGTH: 86
<212> TYPE: RNA
<213> ORGANISM: Artificial
<220> FEATURE:
<223> OTHER INFORMATION: An example of an RNA sequence derived from
      Turnip yellow mosaic virus

<400> SEQUENCE: 1
uuagcucgcc aguuagcgag gucuguccccc acacgacaga uaaucgggug caacucccgc     60
cccuuuuccg agggucaucg gaacca                                           86